(12) United States Patent
Wilger et al.

(10) Patent No.: US 10,959,864 B2
(45) Date of Patent: Mar. 30, 2021

(54) BARBED WIRE STENT

(71) Applicant: Cook Medical Technologies LLC, Bloomington, IN (US)

(72) Inventors: Kevin D. Wilger, Lafayette, IN (US); Ryan C. Bradway, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 87 days.

(21) Appl. No.: 16/245,351

(22) Filed: Jan. 11, 2019

(65) Prior Publication Data

US 2019/0209352 A1    Jul. 11, 2019

Related U.S. Application Data

(60) Provisional application No. 62/616,129, filed on Jan. 11, 2018.

(51) Int. Cl.
| | | |
|---|---|---|
| *A61F 2/848* | (2013.01) | |
| *A61F 2/07* | (2013.01) | |
| *A61F 2/89* | (2013.01) | |
| *A61F 2/86* | (2013.01) | |
| *A61F 2/82* | (2013.01) | |

(52) U.S. Cl.
CPC ............ *A61F 2/848* (2013.01); *A61F 2/07* (2013.01); *A61F 2/86* (2013.01); *A61F 2/89* (2013.01); *A61F 2002/075* (2013.01); *A61F 2002/825* (2013.01); *A61F 2002/8483* (2013.01); *A61F 2002/8486* (2013.01); *A61F 2220/0016* (2013.01); *A61F 2220/0025* (2013.01); *A61F 2220/0075* (2013.01)

(58) Field of Classification Search
CPC ...... A61F 2/86; A61F 2/07; A61F 2/89; A61F 2002/075; A61F 2002/825; A61F 2002/8486; A61F 2220/0016; A61F 2220/0025; A61F 2220/0075
See application file for complete search history.

(56) References Cited

U.S. PATENT DOCUMENTS

| | | | |
|---|---|---|---|
| 5,733,325 | A | 3/1998 | Robinson et al. |
| 5,800,515 | A | 9/1998 | Nadal et al. |
| 6,200,336 | B1 | 3/2001 | Pavcnik et al. |
| 6,280,467 | B1 | 8/2001 | Leonhardt |
| 6,589,275 | B1 | 6/2003 | Ivancev et al. |
| 7,452,371 | B2 | 11/2008 | Pavcnik et al. |

(Continued)

FOREIGN PATENT DOCUMENTS

| | | |
|---|---|---|
| WO | WO 1999/043379 A1 | 9/1999 |
| WO | WO 2004/016201 A2 | 2/2004 |
| WO | WO 2017/036207 A1 | 3/2017 |

OTHER PUBLICATIONS

Communication—Extended European Search Report for EP 19151493.4-1113, dated Jun. 3, 2019.

*Primary Examiner* — George J Ulsh
(74) *Attorney, Agent, or Firm* — Brinks Gilson & Lione (57) ABSTRACT

Disclosed herein is a stent which includes stent ring structures made up of at least one wire and at least one tubular connector through which a portion of the wire is disposed. The tubular connector includes a side wall with an aperture formed therethrough. A portion of the wire extends therethrough and acts as a barb. A method of making such a stent is also disclosed.

18 Claims, 5 Drawing Sheets

(56) References Cited

U.S. PATENT DOCUMENTS

| | | |
|---|---|---|
| 7,815,589 B2 | 10/2010 | Meade et al. |
| 7,905,915 B2 | 3/2011 | Young et al. |
| 8,292,946 B2 | 10/2012 | Thistle et al. |
| 8,409,271 B2 | 4/2013 | Hashimoto et al. |
| 8,668,729 B2 | 3/2014 | Kaufmann et al. |
| 8,870,947 B2 | 10/2014 | Shaw |
| 2004/0117004 A1 | 6/2004 | Osborne et al. |
| 2008/0033534 A1* | 2/2008 | Cook ........................ A61F 2/86 623/1.36 |
| 2009/0171442 A1* | 7/2009 | Young ....................... A61F 2/06 623/1.15 |
| 2013/0073029 A1* | 3/2013 | Shaw ............... A61B 17/12122 623/1.36 |
| 2017/0135830 A1 | 5/2017 | Harkin et al. |

\* cited by examiner

BARBED WIRE STENT

BACKGROUND

The present application generally relates to medical devices. More particularly, the present application relates to a stents and methods of making stents in which a barb may be provided on an end of a wire making up a strut of said stent.

A standard practice in aortic stent grafting is to incorporate barbed stents to prevent migration of the device into the aneurysm sac. Applications of these barbed stents include the suprarenal stents of bifurcated abdominal aortic aneurysm (AAA) grafts, the top stents of fenestrated grafts, and proximal and distal components of thoracic stent grafts, among others.

Barbed stents can be manufactured by soldering barbs to wire stents, by laser cutting into a cannula-cut stent, or by attaching the barb mechanically (such as by crimping or by winding) to the strut or to apices of the strut. In addition, cannula cut barbed stents or other barb attachment methods can be comparably harder to manufacture, or can be more expensive, or can contribute to an increase in the thickness of the strut.

It has been a challenge to develop a barbed stent that is less expensive and simple to manufacture, having superior barb-joining methods, and doing so without significantly increasing the diameter of the strut.

SUMMARY

In one aspect, the present disclosure provides a stent for implantation into a body vessel. The stent may include a first wire extending from a first terminal end to a second terminal end, a body extending from the first terminal end to the second terminal end, and at least one bend in the body. The stent may also include a tubular connector having a first end, a second end, a connector body between the first end and the second end, a lumen, a longitudinal axis, and a side aperture in a wall of the connector body between the first end and the second end. At least one of the first end and the second end may be an open end in fluid communication with the lumen. A portion of the first wire may be disposed in the lumen of the connector and an end of the first wire may be disposed through the aperture and may extend outwardly from the wall of connector. The at least one bend may define a peak of a stent ring.

In another aspect, the present disclosure provides a stent for implantation into a body vessel. The stent may include a first wire extending from a first terminal end to a second terminal end, a body extending from the first terminal end to the second terminal end, with at least one bend in the body. The second terminal end of the wire may define a barb. The stent may include a tubular connector having a first end and a second end, a connector body between the first end and the second end, a lumen, and a longitudinal axis. There may be a side aperture in a wall of the connector body between the first end and the second end. At least one of the first end and the second end may be an open end in fluid communication with the lumen. A portion of the first wire may be disposed in the lumen of the connector, and the barb may be disposed through the aperture of the connector, and may extend outwardly from the connector. The at least one bend may define a peak of a stent ring.

In a further aspect, the present disclosure provides a method of making a stent. The method may include forming a stent ring with a wire and a tubular connector. The wire may extend from a first terminal end to a second terminal end defining a wire body therebetween. The second terminal end may include a barb. The wire body may define at least one bend therein. The tubular connector may have a first end, a second end, a connector body between the first end and the second end, a lumen, and a longitudinal axis. The tubular connector may have a side aperture in a wall of the connector body between the first end and the second end. At least one of the first end and the second end may be an open end in fluid communication with the lumen. The stent ring may be formed such that a portion of the wire is disposed in the lumen of the tubular connector and the barb is disposed through the side aperture of the connector and extends outwardly from the wall of the connector. The at least one bend may define a peak of the stent ring.

Further objects, features and advantages of this system will become readily apparent to persons skilled in the art after a review of the following description, with reference to the drawings and claims that are appended to and form a part of this specification.

DETAILED DESCRIPTION

The drawings are purely schematic illustrations of various aspects of the device and method being described, and are not necessarily to scale, unless expressly stated.

The terms "substantially" or "about" used herein with reference to a quantity includes variations in the recited quantity that are equivalent to the quantity recited, such as an amount that is equivalent to the quantity recited for an intended purpose or function. "Substantially" or derivatives thereof will be understood to mean significantly or in large part. When used in the context of a numerical value or range set forth, "about" or "substantially" means a variation of ±15%, or less, of the numerical value. For example, a value differing by ±15%, ±14%, ±10%, or ±5%, among others, would satisfy the definition of "about" or "substantially."

Figure 1:
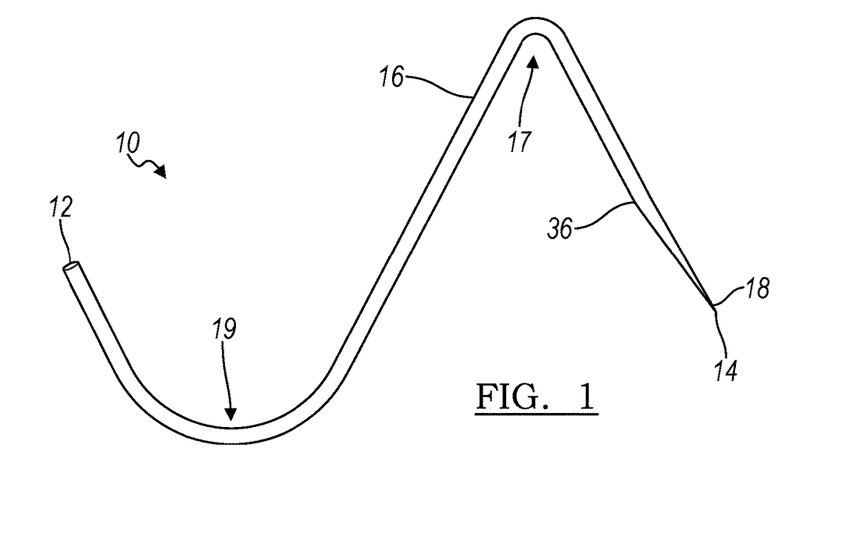
FIG. 1 is a side view of a wire for use in constructing a stent ring in accordance with one embodiment of the present disclosure.

FIG. 1 illustrates a wire 10 that may be used in the construction of a stent ring in accordance with one embodiment of the present disclosure. The illustrated wire 10 extends from a first end 12 to a second end 14 and defines a wire body 16 therebetween. As illustrated in FIG. 1, the wire 10 may terminate in a barb 18; in this case, the second end 14 is sharpened to a point to define the barb 18. The barb 18 may also be bent away from the remainder of the wire body 16 at bend 36.

In some embodiments, the barb 18 could be manufactured by grinding the wire to a point. In some embodiments, the angle of projection of the barb 18 from the wire body 16 may be formed by heat setting the wire body 16 while bent over a mandrel or a ledge.

The wire body 16 as illustrated in FIG. 1 includes a first bend 17 and a second bend 19. When the wire 10 is used in constructing a stent ring, the first bend 17 may define a peak of the stent ring, and the second bend 19 may define another peak of the stent ring (for example, on the opposite end, longitudinally, of the stent ring.)

In the illustrated embodiment, the first bend 17 has a smaller radius of curvature than does second bend 19. In another embodiment in which a wire has multiple bends, all bends may have substantially the same radius of curvature. In other embodiments, a wire for use in a constructing a stent ring may have only a single bend. In other embodiments, a wire may have more than two bends, and each bend may have a different radius of curvature, or any combination of radii of curvature.

A wire 10 for use in constructing a stent ring in accordance with the principles of the present disclosure may be made of a variety of different materials. Because the stent ring is intended to be an intraluminal implant for a body vessel, the wire 10 may be made of a biocompatible material, or may have a coating to improve its biocompatibility. In one embodiment, the wire 10 may comprise steel, such as 304 stainless steel. In another embodiment, the wire 10 may comprise a shape memory material, including a shape memory alloy selected from among a nickel-titanium alloy, a cobalt-chromium alloy, and other suitable alloys as are known in the art.

The wire 10 for use in the stent rings described herein may be manufactured in a number of ways. In an embodiment wherein the wire comprises a shape memory alloy, the wire 10 may be manufactured by heat setting a nitinol wire around a cylindrical mandrel, or in a flat pattern. In another embodiment, a precursor length of wire may be formed into a shape which substantially resembles the finished shape of the intact stent ring, optionally formed and heat set to shape about a mandrel, and then cut into separate segments. The ends of these segments may then be formed into barbs as appropriate.

Figures 2, 3A:
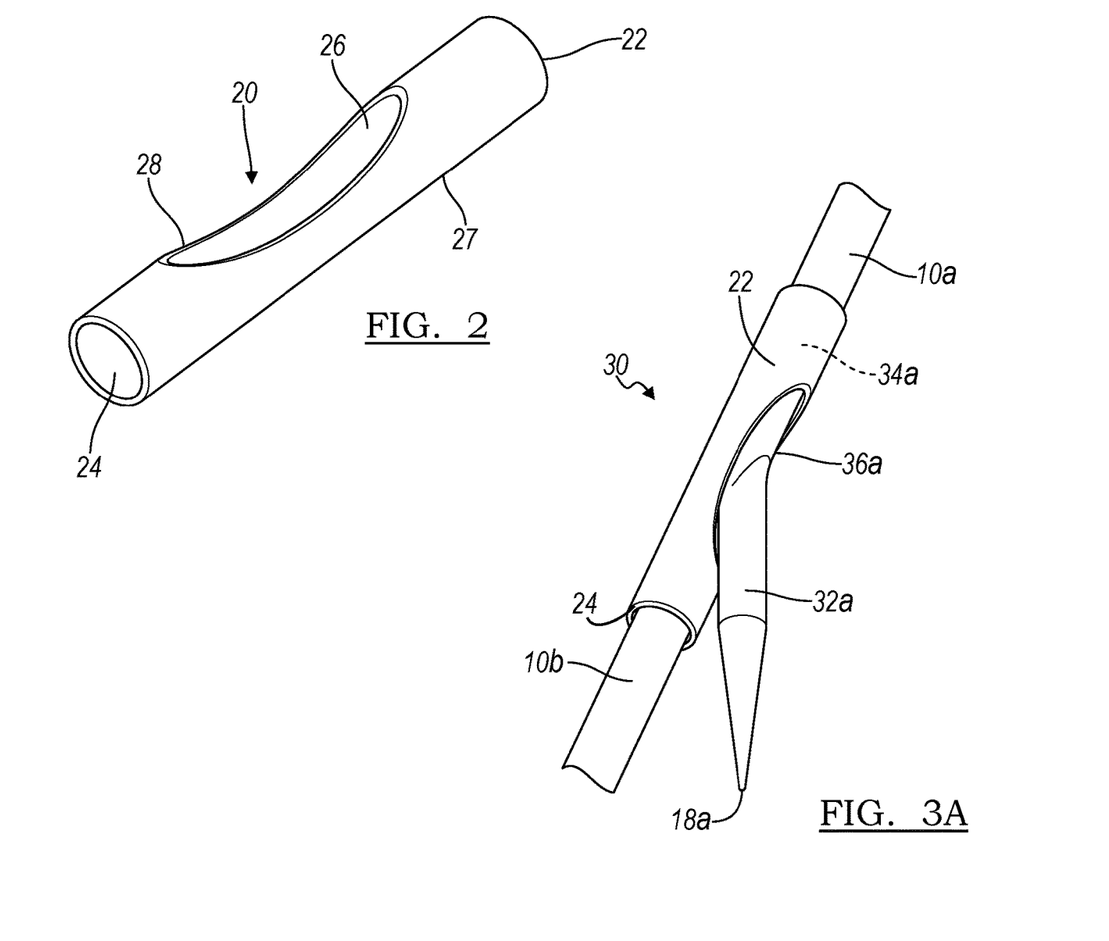
FIG. 2 is a perspective view of a tubular connector in accordance with an embodiment of the present disclosure.
FIG. 3A is a perspective view of an end of a wire extending through a tubular connector in accordance with an embodiment of the present disclosure.

FIG. 2 illustrates a tubular connector 20 constructed in accordance with an embodiment of the present disclosure. The connector 20 extends from a first connector end 22 to a second connector end 24. The body of the connector 20 defines a wall 27 and surrounds a lumen 26 that runs through the body of the connector 20. The connector 20, being a tubular member, also defines a longitudinal axis running therethrough, which passes through the lumen 26 and extends through first connector end 22 and second connector end 22. As with the wire, a tubular connector 20 may be made of any suitable material, including stainless steel, a shape memory material, a polymer, or any other biocompatible material as is known in the art. The tubular connector 20 may be made from a precursor cannula in some embodiments.

The tubular connector 20 also defines at least one side aperture 28 through the wall 27, which is located on the body of the connector 20 between first connector end 22 and second connector end 24. The side aperture 28 can be formed through the wall 27 in a number of ways, including machining, laser cutting, and grinding.

The tubular connector 20 may function to join wires 10 in the assembly of the stent ring. The tubular connector 20 may have at least one open end at first connector end 22 or second connector end 24, or two open ends at both connector ends 22 and 24, in order to facilitate the entry of portions of wires 10. The side aperture 28 of the tubular connector 20 allows for the egress of a portion of the wire 10, such as second end 14 of the wire 10, through the tubular connector 20, in order to form a barb or other protruding portion of the wire 10.

In the embodiment of FIG. 3A, a portion 34a of the first wire 10a extends through first end 22 of the tubular connector 20 into lumen 26, and a portion 32a extends into the including the second end 14a of the wire 10a passes through the side aperture 28 to form barb 18a. A second wire 10b extends through second connector end 24 and into lumen 26, such that tubular connector 20 bridges the two wires 10a/10b.

Figure 3B:
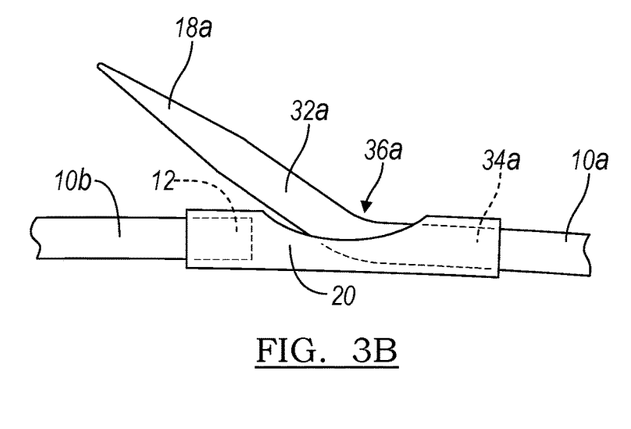
FIG. 3B is a side view of an end of a wire defining a barb extending through a tubular connector in accordance with another embodiment of the present disclosure.

FIG. 3B is another view of the barb 18a and connector 20 of FIG. 3A. As can be seen in FIG. 3B, the wire 10a includes the portion 34a within the connector and the portion 32a which protrudes out from the connector 20 at a defined angle from the path of the strut due to bend 36a. The end 14a terminates at a point to form barb 18a.

The properties of the tubular connector 20 may be adjusted in order to meet the needs of the application for which the implant is to be used. For example, the length of the slotted portion relative to the unslotted portion can be modified according to the location of the barb on the strut, and can be tailored in view of the quantity of barbs to be employed. The overall length of the tubular connector 20 may be adjusted based on the amount of support it will need to provide to the stent structure, and with consideration to the density of material that will be present when the device containing the stent ring is deployed, and so forth.

Figure 3C:
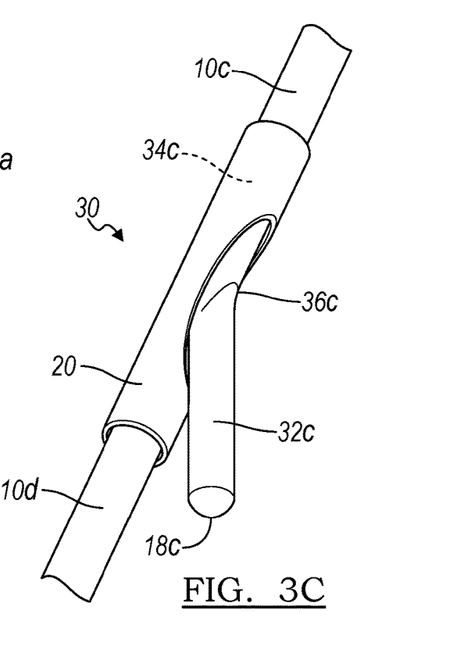
FIG. 3C is a perspective view of the barb depicted in FIG. 3B.

Another embodiment of a wire-and-connector assembly 30 is illustrated in FIG. 3C. As can be seen in FIG. 3C, the wire 10c includes the portion 34c within the connector and the portion 32c which protrudes out from the connector 20 at a defined angle from the path of the strut due to bend 36a. In this embodiment, the portion 32c of the first wire 10c does not terminate in a barb; rather, end 18c is simply the unmodified end of the wire 10c. Such a construct may be useful when the wire 10c is of small enough diameter that the end 18c functions to anchor the stent ring even without sharpening, thereby substantially functioning as a barb.

Although the illustrated embodiments portray wires 10 and tubular connectors of a round cross section, it will be noted that other cross sectional profiles for these components (for example, square-shaped and triangular) may be appropriate for various applications.

Figure 4:
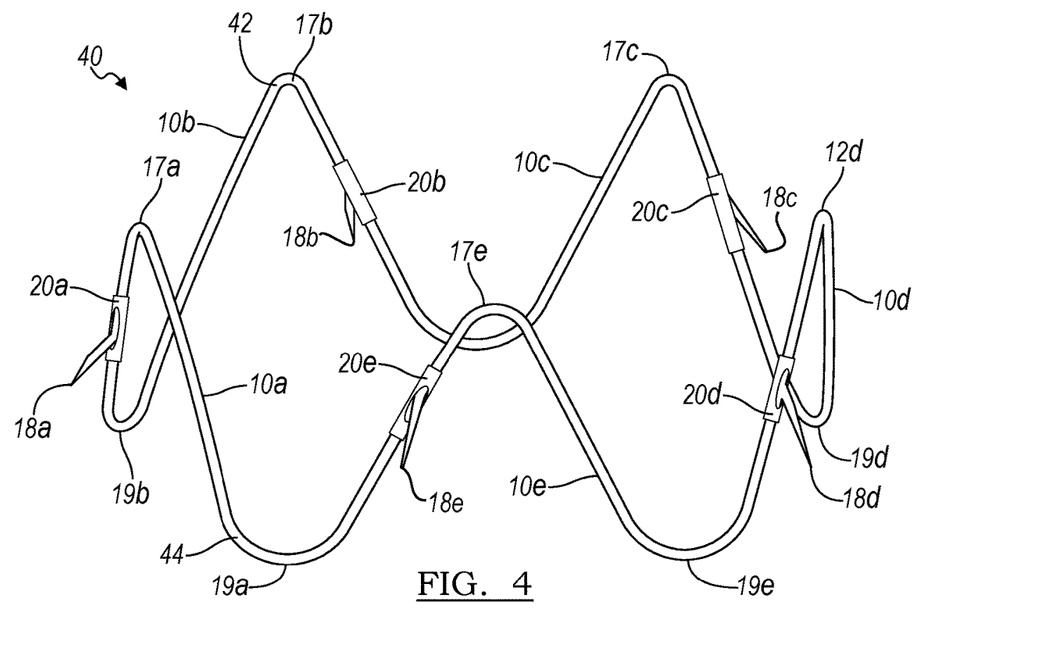
FIG. 4 is a view of a stent ring formed of wires and tubular connectors in accordance with the principles of the present disclosure.

FIG. 4 illustrates a stent ring 40 made up of five wires 10a-e according to an embodiment of the present disclosure. The wires 10a-e are interconnected with one another in the same manner as is illustrated in FIGS. 3A-C. Five wires 10a-e are connected via five tubular connectors 20a-e. The first bends 17a-e represent a series of first peaks 42 of the stent ring 40, and second bends 19a-e represent a series of second peaks 44 of the stent ring 40 on the opposite longitudinal end of the stent ring 40. In some instances, the first peaks 42 may be proximal peaks, and the second peaks may be distal peaks, or vice versa. Each wire has a barb 18a-e extending through a respective connector 20a-e.

The stent ring 40 may be made by fixing the wires into the lumen of the tubular connectors. In one embodiment, the wire may be laser welded to the tubular connector. In another embodiment, a biocompatible adhesive may be used to secure the wire to the tubular connector.

A stent ring 40 as shown in FIG. 4 may be used in a variety of medical implants. In one embodiment, the implant may be a stent. In another embodiment, the implant may be a stent graft. In a particular embodiment, a stent ring 40 as in FIG. 4 may be placed such that it is the end ring of a stent graft. The orientation of the barbs 18a-e, away from the direction in which the end ring of a stent graft would extend, provides anchoring for the stent graft when deployed.

The stent ring 40 as shown in FIG. 4 has five wires 10a-e, five connectors 20a-e, and five barbs 18a-e. Such a stent ring as depicted has five upper peaks 17a-e and five lower peaks 19a-e. It will be appreciated that a stent ring in accordance with the principles of the present disclosure need not have an equal number of wires, peaks, and barbs; that is, in certain cases it may be preferred to have no barb extend from a connector, for instance.

A stent ring 40 made of wires 10 that have a barb 18 formed at the end may yield increased barb fatigue performance compared to other barb attachment methods that involve joining a separate barb to a device, such as soldering. Because the wire and the barb are unitary, the barb, wire, and stent ring may be easier to manufacture, compared to welding or soldering a separate component to the strut or ring.

A stent ring made from wire terminating at an end in a barb may have improved packing density. The combination of a tubular connector with a wire terminating in a barb that extends through a side aperture of the tubular connector may have a lower overall diameter (such as about 0.6 mm) compared to an exemplary laser-cut barb (which may have a diameter of about 1.05 mm).

Making a barb from the end of a precursor piece of wire also allows for adjustable barb lengths and diameters, unlike cannula cut barbs, the dimensions of which are constrained by the length and width of the strut from which they are cut, the barb of a construction according to the principles of the present disclosure can be terminated at various lengths and can be ground down to a variety of diameters.

Figure 5A:
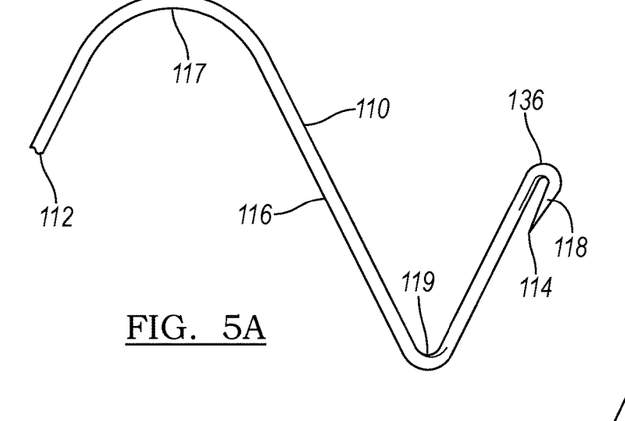
FIG. 5A is a side view of another embodiment of a wire for use in a stent.
Figure 5B:
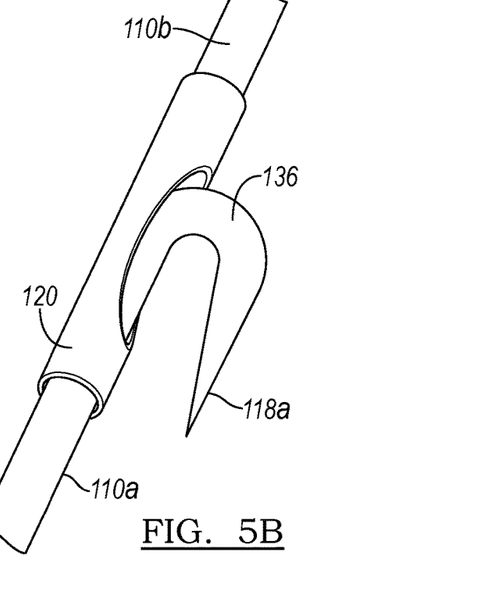
FIG. 5B is a close up view of the barb of the wire of FIG. 5A.
Figure 5C:
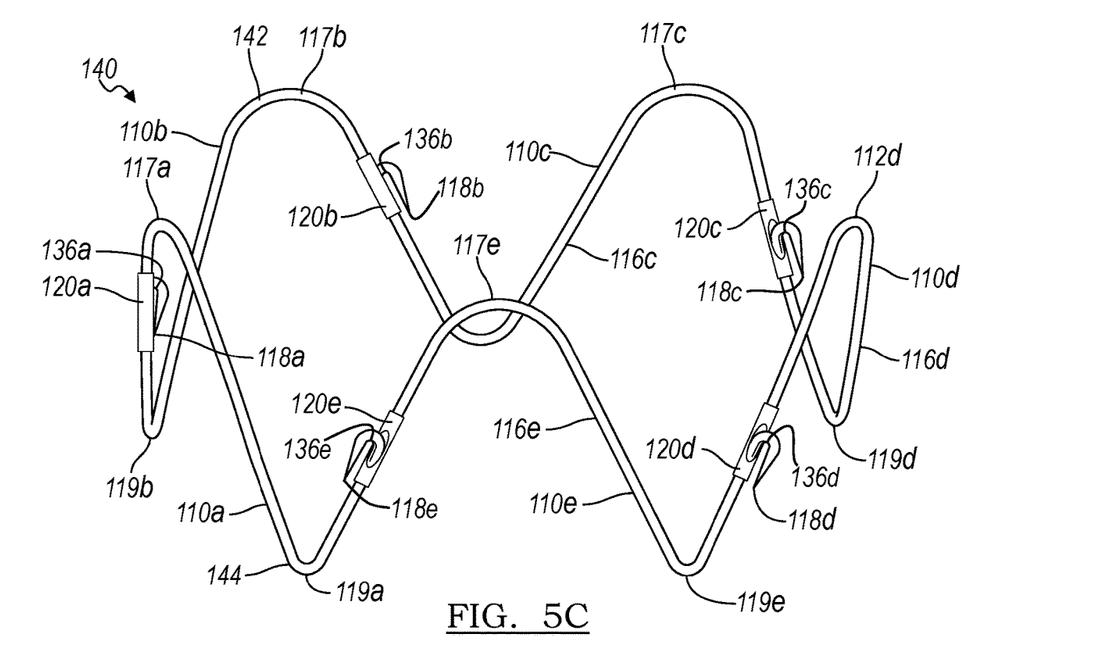
FIG. 5C is a stent ring constructed of wire segments represented in FIG. 5A.

FIG. 5A illustrates another embodiment of a wire 110 in accordance with the principles of the present disclosure. The wire of FIG. 5A resembles that of FIG. 1 in that it has first end 112, second end 114, upper bend 119, lower bend 117, and barb 118, except the bend 136 is a U-shaped looping of the wire body 116. In this embodiment, and as shown in FIG. 5B, the wire 110a may extend through the tubular connector 120, and the barb 118a emerge through the side aperture 128, forming an acute angle relative to the portion of the wire body 116a from which it extends, in contrast to the obtuse angle formed in the wire 10 illustrated in FIG. 1. A stent ring 140 made of wires 110a-e is illustrated in FIG. 5C with five connected wires 110a-e having upper peaks 117a-e, lower peaks 119a-e, connectors 120a-e, bends 136a-e and barbs 118a-e.

Figure 6:
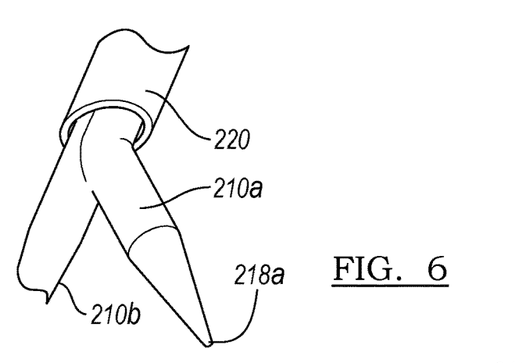
FIG. 6 is a perspective view of a strut arrangement of a stent constructed in a further embodiment of the present disclosure.

FIG. 6 illustrates a connection in accordance with another embodiment of the present invention. In this embodiment, two wires 210 and 210b are crimped together side-by-side in a single tubular connector 220. Wire 210a has barb 218a. The wires themselves may be fused by welding or another attachment mechanism, and the tubular connector 220 may be sized such that the cannula itself is not secured to the wires 210a/210b. The wires 210a/210b may also be attached to one another or to the connector 220 by an adhesive or any other connection mechanism known in the art.

Figure 7A:
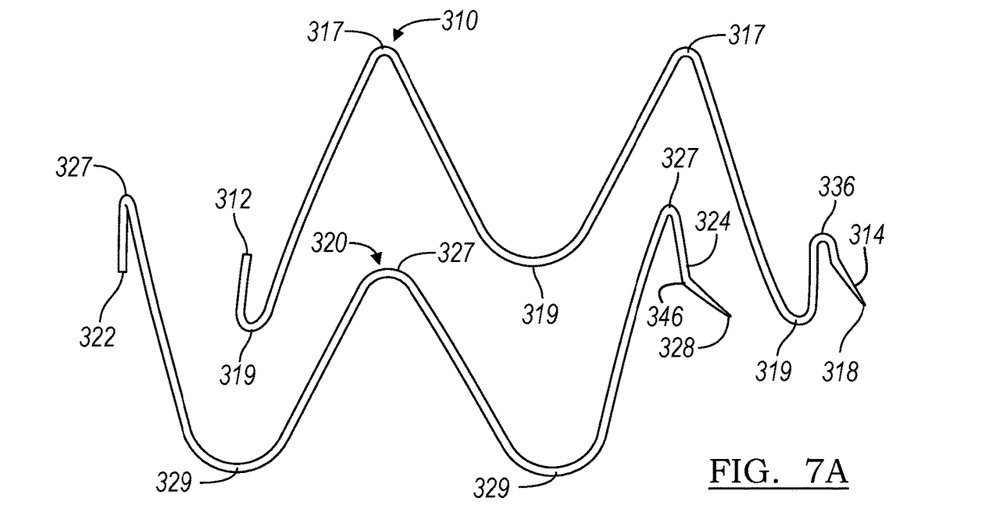
FIG. 7A is a side view of a pair of wire segments for making a stent ring in accordance with the principles of another embodiment of the present disclosure.

FIG. 7A illustrates two wires 310 and 320 according to another embodiment of the present disclosure. Wire 310 has first end 312, a second end 314, bend 336 in the second end 314 and barb 318. Wire 320 has a first end 322, a second end 324, a bend 346 in the second end and a barb 328. As mentioned previously, the number of barbs is not required to match the number of peaks of the stent ring. The wire 310 has two upper peaks 317 and three lower peaks 319, and the wire 320 has three upper peaks 327 and two lower peaks 329, such that when connected by two tubular connectors 340a and 340b, the resultant stent ring 350 has two barbs 318/328, but five upper and lower peaks as in the embodiment of FIG. 4.

Figure 7B:
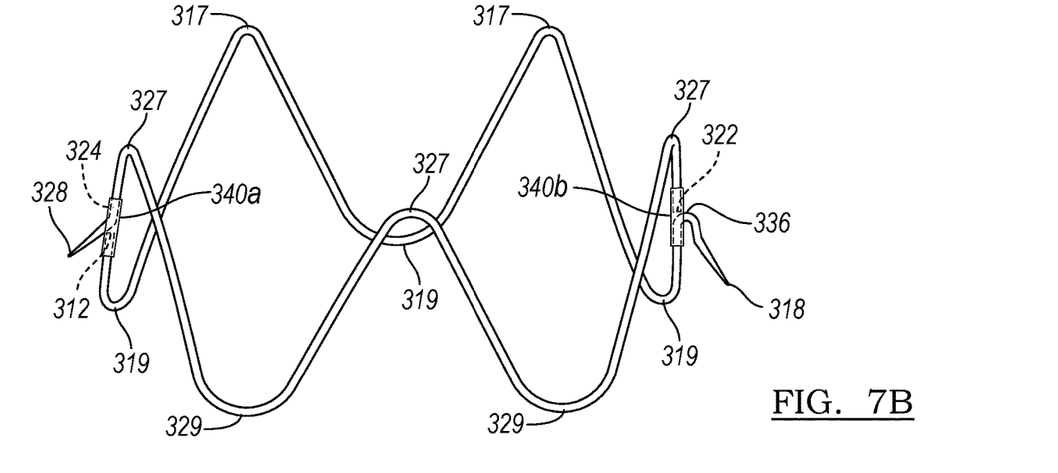
FIG. 7B is a stent ring constructed of the wire segments of FIG. 7A.

FIG. 7B is a stent ring constructed of the wire segments of FIG. 7A. As shown, wires 310 and 320 are connected by connectors 340a and 340b.

Figure 8:
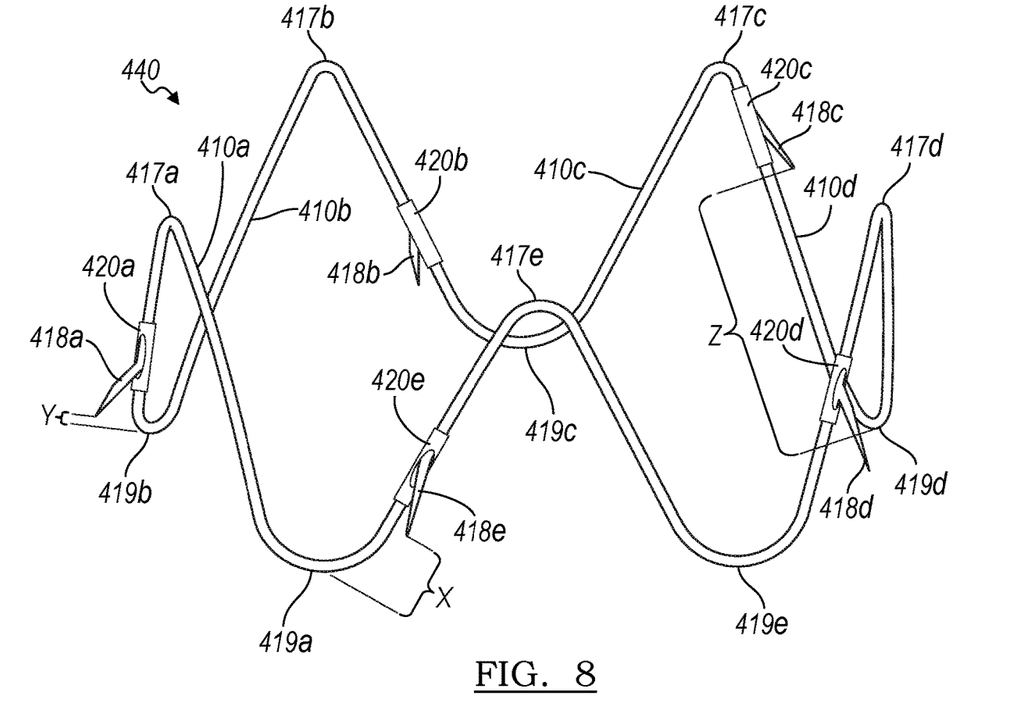
FIG. 8 is a stent ring constructed in accordance with another embodiment of the present disclosure.

FIG. 8 illustrates another embodiment of a stent ring 440. Stent 440 has upper peaks 417a-e, lower peaks 419a-e, struts 410a-d, and barbs 418a-e. In this stent ring 440, the position of tubular connectors 420a-e are varied in the longitudinal dimension. As shown, barb 418a extends such that it terminates at a point which is a distance Y from the lower peak 419b toward which it points. This distance Y is less than a distance X, which is the distance between lower peak 419a and barb 418e. Distance Z, between barb 418c and lower peak 419d, is greater even than distance X. Distributing the connectors in the longitudinal dimension may assist with packing density of the implant when compressed as the connectors increase the diameter of the stent struts.

Figure 9:
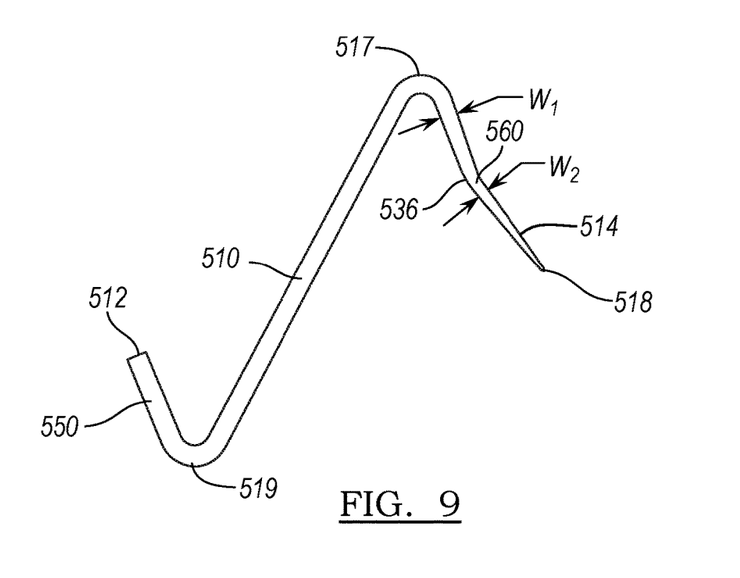
FIG. 9 is a side view of another wire for use in constructing a device in accordance with another embodiment of the present disclosure.

FIG. 9 illustrates another embodiment of a wire 510 that may be employed in the construction of a stent ring. As shown in FIG. 9 the wire 501 has a first end 512, a second end 514, a barb 518, a first bend 517 and a second bend 519. Unlike the wire of FIG. 1, which is substantially constant in diameter along its length except for the barb itself, the wire 510 of FIG. 9 has a thinned zone 560 in which the wire tapers prior to the bend 536. The width $w_1$ of the main portion of the wire 510 is greater than $w_2$ of the thinned zone 560. Such thinning may assist in making a more labile barb for uses in which more flexibility of the barb is desirable.

As a person skilled in the art will readily appreciate, the above description is only meant as an illustration of implementation of the principles this application. This description is not intended to limit the scope of this application in that the system is susceptible to modification, variation and change, without departing from the spirit of this application, as defined in the following claims.

What is claimed is:

1. A stent for implantation into a body vessel, the stent comprising:
    a first wire extending from a first terminal end to a second terminal end, a body extending from the first terminal end to the second terminal end, and at least one bend in the body; and
    a tubular connector having a first end, a second end, a connector body between the first end and the second end, a lumen, a longitudinal axis, and a side aperture in a wall of the connector body between the first end and the second end;

wherein a portion of the first wire is disposed in the lumen of the connector and an end of the first wire is disposed through the aperture and extends outwardly from the wall of connector, and wherein the at least one bend defines a peak of a stent ring; and wherein the first end and the second end of the tubular connector are open ends; and wherein a portion of the first wire is disposed through the first end of the tubular connector, and a portion of a second wire is disposed through the second end of the tubular connector.

2. The stent of claim 1, wherein the end of the wire disposed through the aperture comprises a barb.

3. The stent of claim 1, wherein the stent ring comprises the first wire and a second wire.

4. The stent of claim 3, wherein the stent ring comprises a plurality of tubular connectors.

5. The stent of claim 1, wherein the body comprises a first bend and a second bend, each of the first bend and the second bend defining a peak of the stent ring.

6. The stent of claim 5, wherein the first bend has a first radius of curvature and the second bend has a second radius of curvature, the first radius of curvature being different from the second radius of curvature.

7. The stent of claim 1, wherein the portion extends at an acute angle relative to the longitudinal axis of the tubular connector.

8. The stent of claim 1, wherein the portion is bent to define an obtuse angle relative to the longitudinal axis of the tubular connector.

9. The stent of claim 1, wherein the first wire comprises a shape-memory material.

10. The stent of claim 9, wherein the shape-memory material is selected from a nickel-titanium alloy and a cobalt-chromium alloy.

11. The stent of claim 1, wherein the stent comprises a portion of a stent graft.

12. A stent for implantation into a body vessel, the stent comprising:

a first wire extending from a first terminal end to a second terminal end, a body extending from the first terminal end to the second terminal end, at least one bend in the body, and the second terminal end of the wire defining a barb; and a tubular connector having a first end and a second end, a connector body between the first end and the second end, a lumen, a longitudinal axis, a side aperture in a wall of the connector body between the first end and the second end, wherein at least one of the first end and the second end is an open end in fluid communication with the lumen;

wherein a portion of the first wire is disposed in the lumen of the connector and the barb is disposed through the aperture of the connector and extends outwardly from the connector, and wherein the at least one bend defines a peak of a stent ring.

13. The stent of claim 12, wherein the stent ring comprises a second wire.

14. The stent of claim 13, wherein the stent ring comprises a plurality of tubular connectors.

15. The stent of claim 12, wherein the first wire comprises a first bend and a second bend, each of the first bend and the second bend defining a peak of the stent ring.

16. The stent of claim 12, wherein the first end and the second end of the tubular connector are open ends.

17. The stent of claim 16, wherein a portion of the first wire is disposed through the first end of the tubular connector, and a portion of a second wire is disposed through the second end of the tubular connector.

18. A method of making a stent, the method comprising:
forming a stent ring with a wire and a tubular connector,
the wire extending from a first terminal end to a second terminal end defining a wire body therebetween, the second terminal end comprising a barb, the wire body defining at least one bend therein;

the tubular connector having a first end, a second end, a connector body between the first end and the second end, a lumen, a longitudinal axis, a side aperture in a wall of the connector body between the first end and the second end, wherein at least one of the first end and the second end is an open end in fluid communication with the lumen;

the stent ring being formed such that a portion of the wire is disposed in the lumen of the tubular connector and the barb is disposed through the side aperture of the connector and extends outwardly from the wall of the connector, the at least one bend defining a peak of the stent ring.

* * * * *